USOO5585563A

United States Patent [19]

Bui

[11] Patent Number: 5,585,563
[45] Date of Patent: Dec. 17, 1996

[54] NON-CONTACT THICKNESS MEASUREMENT USING UTG

[76] Inventor: Hoa T. Bui, 372 Church Hill Rd., Trumbull, Conn. 06611

[21] Appl. No.: 94,664

[22] Filed: Jul. 8, 1993

[51] Int. Cl.$^6$ ............................ G01N 29/10; G01N 29/22
[52] U.S. Cl. .................. 73/597; 73/617; 73/644
[58] Field of Search ........................ 73/617, 597, 606, 73/644

[56] References Cited

U.S. PATENT DOCUMENTS

| | | | |
|---|---|---|---|
| 2,697,936 | 12/1954 | Farrow | 73/644 |
| 3,529,465 | 9/1970 | Kleesattel et al. | 73/644 |
| 3,596,505 | 8/1971 | Zeutschel | 73/644 |
| 3,690,154 | 9/1972 | Wells et al. | 73/617 |
| 3,747,398 | 7/1973 | Rathburn et al. | 73/617 |
| 4,898,034 | 2/1990 | Kupperman et al. | 73/644 |
| 5,009,103 | 4/1991 | Sato et al. | 73/597 |
| 5,271,274 | 12/1993 | Khuri-Yakub et al. | 73/597 |

*Primary Examiner*—Sandra L. O'Shea
*Assistant Examiner*—Rose M. Finley

[57] ABSTRACT

A measurement structure for determining the thickness of a specimen without mechanical contact but instead employing ultrasonic waves including an ultrasonic transducer and an ultrasonic delay line connected to the transducer by a retainer or collar. The specimen, whose thickness is to be measured, is positioned below the delay line. On the upper surface of the specimen a medium such as a drop of water is disposed which functions to couple the ultrasonic waves from the delay line to the specimen. A receiver device, which may be an ultrasonic thickness gauge, receives reflected ultrasonic waves reflected from the upper and lower surface of the specimen and determines the thickness of the specimen based on the time spacing of the reflected waves.

7 Claims, 1 Drawing Sheet

NON-CONTACT THICKNESS MEASUREMENT USING UTG

The invention described herein was made in performance of work under NASA contract No. NAS8-37710, and is subject to the provisions of Section 305 of the National Aeronautics and Space Act of 1958, as amended (42 USC 2457).

BACKGROUND OF THE INVENTION

The present invention relates to measurement apparatus and more particularly to a structure for measuring the thickness of a specimen using non-contact techniques.

In the manufacture of a certain class of specimens such as optical lenses and optical coating it is necessary during and at the end of the manufacturing process to determine the thickness of the optical specimen.

Typically, measurements of optical lenses and coatings are made using a mechanical micrometer during and at the end of the manufacturing process. The micrometer must be brought in contact with the optical specimen and this frequently results in damage, such as scratches to the specimen. Also, the accuracy of the measurement made by the micrometer is not ideal, being only within the range of ±2.5 microns.

SUMMARY OF THE INVENTION

An object of the present invention is to provide an improved measurement structure to measuring optical specimens.

Another object of the present invention is to provide a measurement structure for measuring the thickness of optical specimens with improved accuracy without mechanically contacting the specimens.

DESCRIPTION OF A PREFERRED EMBODIMENT OF THE INVENTION

The present invention is a measurement structure for determining the thickness of a specimen without mechanical contact but instead employing ultrasonic waves.

Figure 1:
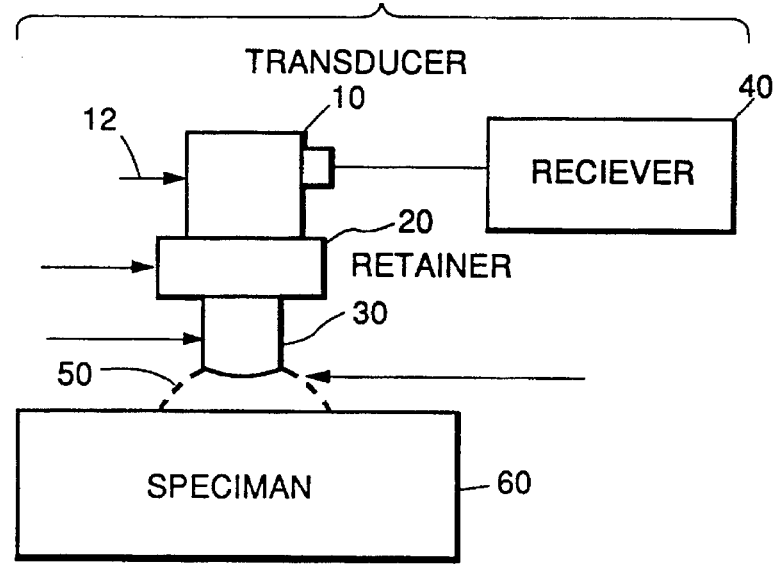
FIG. 1 is a schematic block diagram of an embodiment of a non-contact thickness measurement structure for optical specimens.
Figure 2:
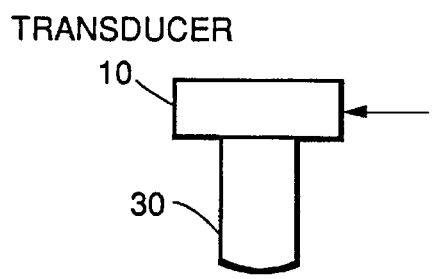
FIG. 2 is a more detailed illustration of the delay line used in the measurement structure of FIG. 1.

Referring to FIG. 1, an embodiment of the present invention is shown including an ultrasonic transducer 10. An ultrasonic delay line 30 is provided that is connected to the transducer 10 by a retainer or collar 20. The specimen 60, whose thickness is to be measured, is positioned below the delay line 30. On the upper surface of specimen 60 a medium such as a drop of water 50 is disposed which functions to couple the ultrasonic waves from the delay line 30 to the specimen 60. A receiver device 40 is also included in the structure. The receiver may be an ultrasonic thickness gauge that receives reflected ultrasonic waves and determines the thickness of a specimen based on the time spacing of the reflected waves.

In operation, an electrical signal is applied to transducer 10 on lead 12 causing ultrasonic waves to be produced which propagate through delay line 30. The ultrasonic waves pass through the interface between the delay line 30 and the medium 50 and then through the medium 50 into the specimen 60. As previously mentioned, the medium 50 may be a drop of water and the specimen 60 may be an optical element such as a minor or a lens, or an optical coating or similar specimen having a thickness to be measured. The optical specimen 60 may also be flat or curved.

Figure 3:
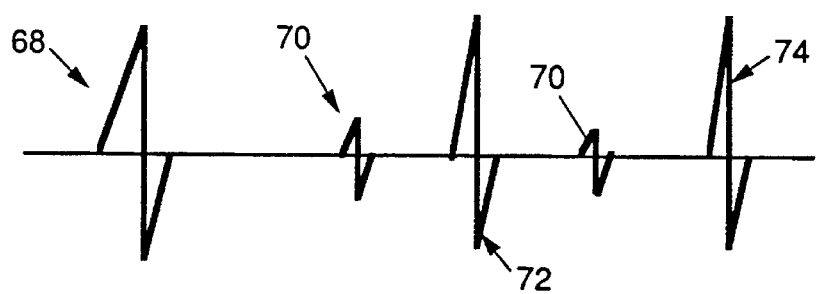
FIG. 3 is an illustration of a waveform showing the signal reflections obtained using the measurement structure of FIG. 1.

As the ultrasonic waves propagate through the delay line 30, water 50 and specimen 60 they are reflected. Referring to FIG. 3 an illustration is provided showing the ultrasonic reflections as a function of time. The first reflection 68 is a reflection of the ultrasonic signal at the transducer 10 and delay line 30. Reflection 70 represents the reflection wave of the ultrasonic signal at the delay line 30 and water 50. The reflection 72 is the reflection wave of the ultrasonic signal at the water and the first (upper) surface of the optical element. The reflection 74 is the reflection wave at the second (lower) surface of the optical element 60.

The reflection signals are applied, via transducer 10, to the ultrasonic thickness gauge 40 that determines the thickness of the optical element based on the time between the reflection 72 from the upper surface of the element and the reflection 74 from the lower surface of the element.

It is important that other signals beside the two signals from the upper and lower specimen surfaces be eliminated to avoid false measurements. The means that the reflection wave 70 caused by this interface between the delay line 30 and the water 50 be eliminated or reduced. This is accomplished by making the lower surface of the delay line 30 curved, such as with a radius of curvature of 25 millimeters. The curvature of the end of the delay line 30 causes the reduction of the reflection wave 70 because the curvature of the end of the delay line may focus the reflection portion of the signal from the water out of the range of the transducer 10 and thickness gauge 40. The range of the curvature, that is the range of radii of curvature for the end of delay line 30 is determined by the radii which focus the interface reflection waves out of the range of the thickness gauge.

In a typical embodiment as shown in FIG. 1, the specimen 60, an optical element, is made level with the delay line 30 and transducers 10 positioned as illustrated. The delay line 30 may be approximately 2 millimeters above the upper surface of the optic element 60 and the gap therebetween filled with water 50 or suitable fluid such as a material known as conplant fluid available from Krantkrammer Branson Co.

An ultrasonic signal is generated by transducer 10 in response to a signal on line 12 of approximately 15 megahertz. The ultrasonic signal propagates through delay line 30, fluid 50 and the optical element 60 and reflection waves, as illustrated in FIG. 3, are returned and applied to the ultrasonic thickness gauge 40. The thickness of the optical element 60 will be determined by gauge 40 according to the following relationship:

$$T = \tfrac{1}{2} v (\text{t.o.f.})$$

where

T: thickness of optical element 60
v: velocity of sound in optical element material
t.o.f.: the time of flight of the reflected waves from the first (upper) surface and the second (lower) surface of optical element 60. The time is obtained from the thickness gauge which includes a clock.

The components used in combination in the embodiment of the invention are all available in the art. The ultrasonic transducer 10 may be a KB UTG CL304, P/N 021-002-823 and ultrasonic thickness gauge 40 may be a Krantkrammer Branson (KB) acoustic probe, 15 MHz Alpha-2 DFR, P/N 113-527-660. This transducer can produce an ultrasonic signal of 15 MHz.

What has been described is a measurement apparatus RF phase for determining the thickness of a specimen, and in particular a non-contact measurement apparatus using ultrasonic techniques which incorporates an ultrasonic transducer, a delay line and an ultrasonic thickness gauge.

While the invention has been described in connection with a preferred embodiment, it is not intended to limit the scope of the invention to the particular form set forth, but, on the contrary, it is intended to cover such alternatives, modifications, and equivalence as may be included within the spirit and scope of the invention as defined in the appended claims.

I claim:

1. A measurement system for non-contact measurement of the thickness of a specimen comprising:

a specimen having a thickness dimension between an upper and a lower surface, means for producing an ultrasonic signal having a selected frequency, a quantity of liquid disposed on said upper surface of said specimen, signal transmission means connected to said ultrasonic signal producing means and in contact with said liquid for the transmission of said ultrasonic signal into said liquid wherein said ultrasonic signal is transmitted through said liquid and said specimen and wherein said ultrasonic signal transmitted through said specimen is reflected from said upper and lower surfaces of said specimen and returns through said liquid and said signal transmission means, and a receiver means responsive to said ultrasonic signals reflected from said upper and lower surfaces of said specimen for determining the thickness of said specimen as a function of the time difference between said ultrasonic signals reflected from said upper and lower surfaces of said specimen, wherein said signal transmission means includes an arcuate surface in contact with said quantity of liquid, and wherein said arcuate surface of said signal transmission means has a radius wherein reflections produced by the interface of said signal transmission means and said quantity of liquid are focused out of the range of said receiver means.

2. A measurement system according to claim 1 wherein said receiver means is an ultrasonic thickness gauge.

3. A measurement system according to claim 1 wherein said liquid is water.

4. A measurement system according to claim 1 wherein said signal transmission means is a delay line.

5. A measurement system according to claim 1 wherein said liquid is water and said selected frequency of said ultrasonic signal is 15 MHz.

6. A measurement system according to claim 4 wherein said specimen is an optical element.

7. A measurement system according to claim 6 wherein said ultrasonic thickness gauge includes a clock means and determines the thickness of said optical element in accordance with the calculation $$T = \tfrac{1}{2} v \cdot (\text{t.o.f.})$$

where:

T is the thickness of said optical element, v is the velocity of sound in said optical element and t.o.f. is the time of flight of the reflected waves from said upper surface and lower surface of said optical element.

\* \* \* \* \*